United States Patent
Fukuda

(10) Patent No.: US 6,532,384 B1
(45) Date of Patent: Mar. 11, 2003

(54) BIOELECTRICAL IMPEDENCE MEASURING METHOD AND BODY COMPOSITION MEASURING APPARATUS

(75) Inventor: Yoshinori Fukuda, Tokyo (JP)

(73) Assignee: Tanita Corporation, Tokyo (JP)

( * ) Notice: Subject to any disclaimer, the term of this patent is extended or adjusted under 35 U.S.C. 154(b) by 0 days.

(21) Appl. No.: 09/653,990

(22) Filed: Sep. 1, 2000

(30) Foreign Application Priority Data

Sep. 3, 1999 (JP) .......................................... 11-250101

(51) Int. Cl.[7] ................................................ A61B 5/05
(52) U.S. Cl. ..................................... 600/547; 600/587
(58) Field of Search ................................. 600/382, 547, 600/587; 177/245; 324/691–694

(56) References Cited

U.S. PATENT DOCUMENTS

| | | | | |
|---|---|---|---|---|
| 4,831,324 A | * | 5/1989 | Asakura et al. | 324/615 |
| 4,911,175 A | * | 3/1990 | Shizgal | 600/547 |
| 5,449,000 A | * | 9/1995 | Libke et al. | 600/547 |
| 6,088,615 A | * | 7/2000 | Masuo | 600/547 |
| 6,243,651 B1 | * | 6/2001 | Masuo | 702/19 |
| 6,256,532 B1 | * | 7/2001 | Cha | 600/547 |
| 6,280,396 B1 | * | 8/2001 | Clark | 600/547 |

FOREIGN PATENT DOCUMENTS

| | | |
|---|---|---|
| JP | 9-154829 | 6/1997 |
| WO | WO 9608198 A1 | 3/1996 |

OTHER PUBLICATIONS

24th Annual Meeting of USGEB in Lausanne/Mar. 25–26, 1993, "Assessment of Limbs and Trunk Composition Using Segmental Bioelectrical Resistance in Man", D. Bracco et al., Internet. J. Vit. Nutr. Res. 63 (1993), p. 241.

European Search Report dated Dec. 7, 2000.

"Triple–Frequency Electroimpedance Method for Evaluation of Body Water Compartments", Tadeusz Nawarycz et al., Medical & Biological Engineering & Computing, vol. 34, Supplement 1, Part 2, 1996, pp. 181–182.

"Bioimpedance Spectrometry in the Determination of Body Water Compartments: Accuracy and Clinical Significance", B.J. Thomas et al., Appl. Radiat. Istot, vol. 49, No. 5/6, 1998, pp. 447–455.

"Triple–frequency method for measuring blood impedance", Tian–xian Zhao et al., Physiol. Meas. 14 (1993), pp. 145–156.

"BIS (Bioelectrical Impedance Spectroscopy)", Attractions of the BIS, SPECTRA & NIR2001 Joint Seminar, Apr. 11, 1998 and English translation, pp. 1–13.

* cited by examiner

Primary Examiner—Kevin Shaver
Assistant Examiner—Charles Marmor, II
(74) Attorney, Agent, or Firm—McDermott, Will & Emery

(57) ABSTRACT

In a bioelectric impedance measuring method of the present invention, a first, second and third bioelectrical impedance values are determined by a measurement using alternating currents having a first, second and third frequencies respectively. Then, an vector impedance locus is derived from only the derived first, second and third bioelectrical impedance values to determine the bioelectrical impedance values at 0 frequency and at an infinite frequency. The body composition is also judged based on the measured results.

Limiting frequencies used for the measurement to three kinds enables the apparatus to be simplified and to be manufactured at a low cost as well as achieving shortened measuring time and enhanced measuring accuracy.

11 Claims, 8 Drawing Sheets

FIG. 6

PARAMETER INPUT

ID      :009876

SEX:    MALE

AGE:

HIGHT:          cm

WIGHT:          kg

FIG. 7

MEASURED RESULTS

Ro/Re:   Ω    ECW:   ℓ
Rinf:    Ω    ICW:   ℓ
Ri:      Ω    TBW:   ℓ
Rc:      Ω    FFM:   kg
Xc:      Ω    FM:    kg

BIOELECTRICAL IMPEDENCE MEASURING METHOD AND BODY COMPOSITION MEASURING APPARATUS

BACKGROUND OF THE INVENTION

1. Field of the Invention

The present invention relates to a bioelectrical impedance measuring method and a body composition measuring apparatus.

2. Description of the Prior Art

An electrical impedance of a living body is typically represented by a lumped constant equivalent circuit comprising an extra-cellular fluid resistance Re, an intra-cellular fluid resistance $R_i$, and a cell membrane capacitance Cm, as shown in FIG. 1. Practically, plural cells making up the living body are respectively represented by individual circuits having different constants due to their different shapes and characteristics. Thus, in the living body as an aggregation of such cells, its vector impedance locus does not show a half circle at variance with the case of measuring the lumped constant equivalent circuit, but shows a circular arc given in the Cole-Cole model.

Thus, the electrical impedance of the living body is generally represented by a circular arc-like locus shown in FIG. 2. In FIG. 2, x-axis represents a resistance component of the impedance, while y-axis represents a reactance component of the impedance. Since the reactance component of the bioelectrical impedance shows a negative value due to its capacitive property, the vector locus of the bioelectrical impedance is plotted on the underside of the real axis as shown in FIG. 2.

Referring to FIG. 3, $R_0$, $R_{inf}$, and Zc respectively indicate a resistance at 0 frequency, a resistance at infinite frequency and a bioelectrical impedance value at frequency Fc. As to $R_0$ and $R_{inf}$, they have only a resistance component because their reactance value is zero. At the frequency Fc, an absolute value of the reactance component reaches its maximum, and Zc is a bioelectrical impedance value at this frequency. As used herein, the frequency where the absolute value of the reactance component reaches its maximum is referred as to a characteristic frequency. Each body composition, such as a total body water, an intra-cellular water, an extra-cellular water, and a fat-free mass, is derived from the above values or approximate values thereof.

In a conventional method for determining the bioelectrical vector impedance locus based on bioelectrical impedances measured at a plurality of frequencies, the bioelectrical impedance is firstly measured in the range from a low frequency to a high frequency (i.e. from several kHz to about 1 MHz). Then, the aforementioned circular arc-like vector locus is derived from the measured data to calculate the above parameters.

Generally, the impedance vector measured by the conventional method is not provided in the form of a circular arc shown by a solid line in FIG. 2, but is represented in a curve-like locus shown by a dotted line in FIG. 2. This is supposedly resulted from a time lag in a signal transmission system which is influenced by both lengths of a bioelectrical impedance measuring cable and a measuring object. Practically, the least square approximation method would be applied to correct such an error and to make the vector impedance locus approximate to the circular arc. Making an approximate calculation requires multiplicity of iterative operations and thereby demands a high-speed arithmetic unit and a peripheral device thereof.

Thus, the conventional bioelectrical impedance measuring apparatus needs to employ the high speed arithmetic unit and the associated peripheral device. In addition, since it takes a long time for the measurement, a patient is forced to keep a specified posture for a long time. This has applied a certain burden to the patient.

An object of the present invention is to provide an improved bioelectrical impedance measuring method and a body composition measuring apparatus, which is capable of solving the problems of the prior art described above.

SUMMARY OF THE INVENTION

According to an aspect of the present invention, there is provided a bioelectrical impedance measuring method for measuring a bioelectrical impedance of a patient by applying an alternating current to a body of the patient, said bioelectrical impedance measuring method comprising the steps of:

determining a first bioelectrical impedance value by a measurement using the alternating current having a first frequency;

determining a second bioelectrical impedance value by a measurement using the alternating current having a second frequency;

determining a third bioelectrical impedance value by a measurement using the alternating current having a third frequency; and deriving a vector impedance locus from only the first, second and third bioelectrical impedance values to determine bioelectrical impedance values at 0 frequency and at an infinite frequency.

According to an embodiment of the present invention, all the first, second and third frequencies may be in the range of 1 kHz to 100 kHz.

According to another aspect of the present invention, there is provided a body composition measuring apparatus for measuring a bioelectrical impedance of a patient by applying an alternating current to a body of the patient based on the bioelectrical impedance method, said body composition measuring apparatus comprising:

an alternating current generating device capable of generating at least three kinds of alternating currents with different frequencies;

a measuring device which determines a first bioelectrical impedance value, a second bioelectrical impedance value and a third bioelectrical impedance value based on measurements using the alternating current having a first frequency, the alternating current having a second frequency and the alternating current having a third frequency respectively, among the alternating currents generated by the alternating current generating device;

an arithmetic device which derives a vector impedance locus from only the determined first, second and third bioelectrical impedance values to determine bioelectrical impedance values at 0 frequency and at an infinite frequency; and a judging device which judges the body composition of the patient based on the bioelectrical impedance values determined by the arithmetic device.

According to another embodiment of the present invention, said body composition measuring apparatus further comprises:

an input device which sets a personal parameter including a body weight of the patient; and an indicating device which indicates information regarding the body composition judged by said judging device, wherein said judging device takes the personal parameter input by the input device into account when judging the body composition of the patient.

According to another embodiment of the present invention, the body composition measuring apparatus may further comprise:

a body weight measuring device which measures the body weight of the patient;

an input device which sets a personal parameter other than the body weight of the patient; and an indicating device which indicates information regarding the body composition of the patient judged by said judging device, wherein said judging device takes the body weight measured by the body weight measuring device and the personal parameter input by the input device into account when judging the body composition of the patient.

According to another embodiment of the present invention, in the body composition measuring apparatus, all the first, second and third frequencies may be in the range of 1 kHz to 100 kHz.

According to another embodiment of the present invention, in the body composition measuring apparatus, the body composition may be at least one of an extra-cellular water, an intra-cellular water, a total body water, a fat-free mass, and a body fat mass.

The present invention will now be described in further detail with regard to preferred embodiments as illustrated in the accompanying drawings.

DESCRIPTION OF THE PREFERRED EMBODIMENTS

Referring to the attached drawings, especially to FIGS. 4 to 10, aspects and embodiments of the present invention will be described in detail.

Figure 4:
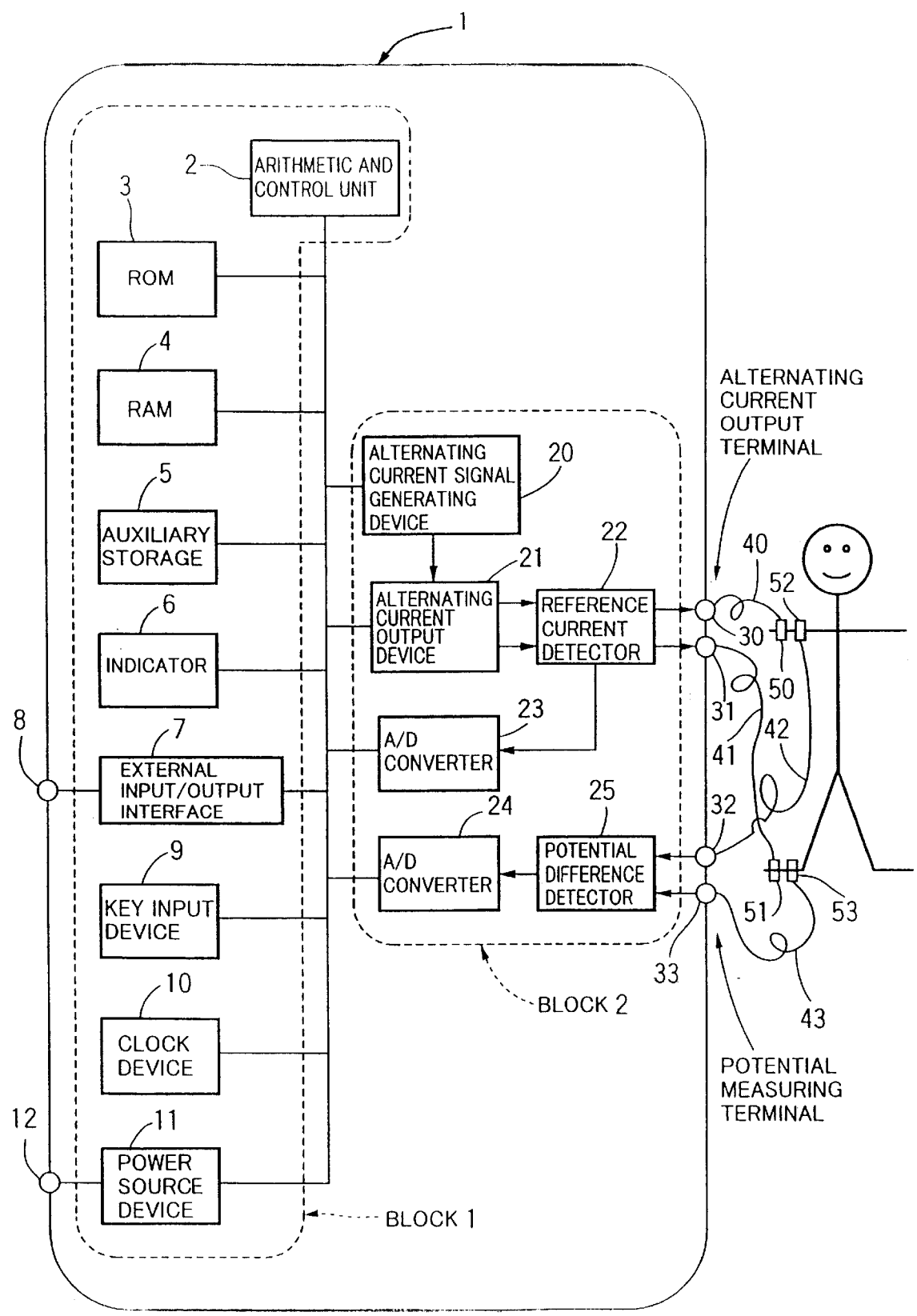
FIG. 4 is a schematic block diagram illustrating a general configuration of a body composition measuring apparatus for executing a bioelectrical impedance measuring method according to an embodiment of the present invention.

FIG. 4 illustrates a general configuration of a body composition measuring apparatus implementing a bioelectrical impedance measuring method according to an embodiment of the present invention. As shown in FIG. 4, the body composition measuring apparatus 1 of the present invention is generally segmented into two blocks, i.e. a block 1 and a block 2.

The block 1 is configured to mainly perform a control for the measurement, an arithmetic operation and an input/output of the data. The block 1 comprises: an arithmetic and control unit 2; a ROM 3 for storing constants and programs for an apparatus control and the arithmetic operation; a RAM 4 for temporarily storing a measured data; an arithmetic result, and data and programs read out from an external device; a nonvolatile auxiliary storage 5 allowing the measured data, the arithmetic result and a parameter regarding the measurement to be stored, read out or updated; an indicator 6 for indicating an information for operation, a condition during measurement, the measured data and the arithmetic result; an external input/output interface 7 for reading a parameter regarding the measurement for an external device and a control information or a control program for the measurement in order to input them into the present apparatus; an external interface terminal 8 for connecting the external input/output interface 7 to the external device; a key input device 9 for inputting a control command for the apparatus and a personal parameter of a person to be measured or a patient; a clock device 10 for generating a time information for controlling a data and time of the measurement; a power source device 11 for supplying an electricity to each part of the present apparatus; and a power source terminal 12 for supplying the electricity to the power source device 11 from an external source.

The block 2 is configured mainly to measure the bioelectrical impedance and to convert an analog signal thereof into a digital signal. The block 2 comprises an alternating signal generating device 20 for generating an alternating current signal with a frequency defined by a control program stored in the ROM 3 or the RAM 4; an alternating current output device 21 for applying to an object to be measured the alternating signal output from the alternating signal generating device 20 with an effective value defined by the control program stored in the ROM 3 or the RAM 4; a reference current detector 22 for detecting a current applied to the object to be measured and for outputting it as a reference current detection signal; alternating current output terminals 30 and 31 which are output terminals for applying to the object to be measured an alternating current supplied from the alternating current output device 21 through the reference current detector 22; an A/D converter 23 for converting an analog signal, which is an output of the reference current detector 22, to a digital signal; potential measuring terminals 32 and 33 which are input terminals for inputting potential signals from the object to be measured at two points thereof respectively; a potential difference detector 25 for outputting a differential signal of the potential signals between the potential measuring terminals 32 and 33; and an A/D converter 24 for converting an analog signal, which is an output of the potential difference detector 25, to a digital signal.

FIG. 4 shows a case where the bioelectrical impedance is measured between a hand and a foot of the patient or the object to be measured by the use of the apparatus having a configuration described above. As for a place to which an electrode for measurement is attached, a well-known conventional manner is employed. As for the hand, an electrode 50 for applying a measuring current connected to the alternating current output terminals 30 via a measuring cable 40 is attached to a back of the hand at a place close to a finger joint. In addition, a potential measuring electrode 52 is connected to the potential measuring terminals 32 via a measuring cable 42 is attached close to a wrist joint. As for the foot, an electrode 51 for applying a measuring current connected to the alternating current output terminals 31 via a measuring cable 41 is attached to an instep of the foot at a place close to a toe joint. In addition, a potential measuring electrode 53 connected to the potential measuring terminal 33 via a measuring cable 43 is attached close to an ankle joint.

Figure 5:
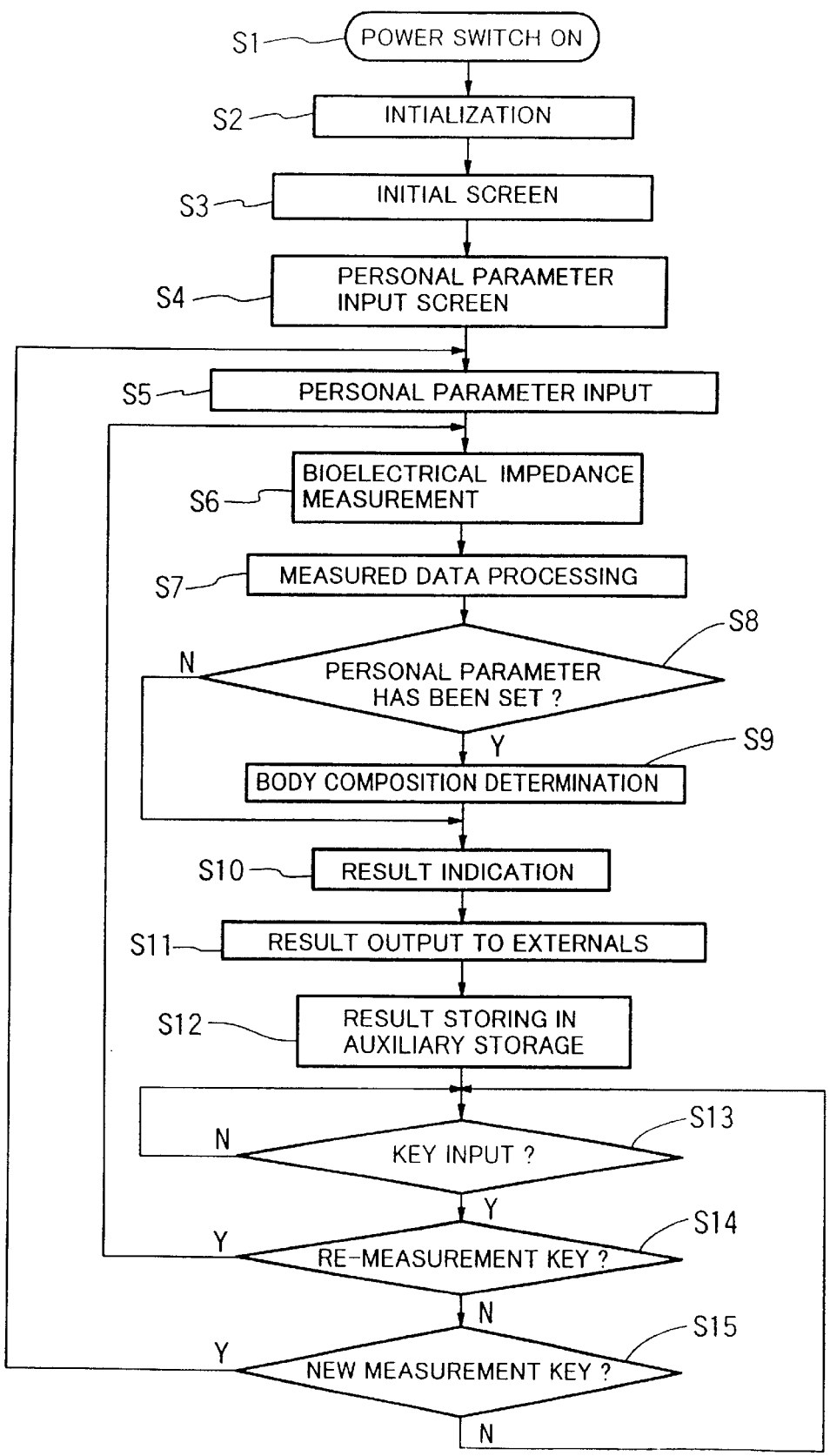
FIG. 5 is a flow chart illustrating a measuring procedure of the apparatus of FIG. 4, FIG. 6 exemplifies an input screen of the apparatus of FIG. 4, FIG. 7 exemplifies a result screen of the apparatus of FIG. 4.

Then a measuring procedure and an operation of the present embodiment will be generally described with reference to the flow chart shown in FIG. 5.

When a power switch of the apparatus is turned on at step S1, the apparatus is initialized (step S2) and simultaneously an initial screen is indicated on the indicator 6 for a few seconds (step S3). Then, at step S4, a screen for inputting a personal parameter shown in FIG. 6 is indicated on the indicator 6 to enter a wait state. At step S5, an identification number of a person to be measured and the personal parameters thereof including a sex, a height, a body weight and an age are input through the key input device 9. The present embodiment is configured, however, such that the measuring can be performed even if these parameters are not set. When the personal parameters are not set, however, an arithmetic operation for calculating a body composition is not executed as described later (step 8).

At step S6, a measuring operation of the bioelectrical impedance starts when a measuring start key is pushed whether or not the personal parameters have been set. It is a matter of course that the electrode for the measurement should have been attached to the person to be measured and should have been connected to the apparatus before starting the measurement.

The bioelectrical impedance is measured according to a following procedure (step S7).

An output signal frequency is set by the alternating signal generating device 20 based on a measurement control parameter stored in advance in the ROM 3 or on the measurement control parameter set in the RAM 4 through the auxiliary storage 5 or the external input/output interface 7. An output signal from the alternating signal generating device 20 is input to the alternating current output device 21.

The alternating current output device 21 is composed of a constant current output circuit whose current value can be optionally set. When the output current value is set based on the measurement control parameter, the alternating current output therefrom is applied to the person to be measured through the reference current detector 22, the alternating current output terminals 30 and 31, the measurement cables 40 and 41 connected to respective terminals, and the electrodes 50 and 51 for applying a measuring current.

At that time, the current applied to the person to be measured is detected by the reference current detector 22. The detected output taking the form of analog signal is converted to the digital signal by the A/D converter 23, and the resulting signal is stored in the RAM 4. Simultaneously, potential signals are input through the potential measuring electrodes 52 and 53 attached to the person to be measured, the measuring cables 42 and 43 connected to respective electrodes, and the potential measuring terminals 32 and 33 connected to respective measuring cables, to the potential difference detector 25. The potential difference detector 25 in turn outputs the potential difference signal, which corresponds to the difference between the potentials input to the potential difference detector, into the A/D converter 24. The A/D converter 24 converts the input analog signal into the digital signal and the resulting signal is stored in the RAM 4.

This process is applied based on the measurement control parameter to each of the alternating currents with the first, second and third frequencies respectively. To achieve a higher accuracy, the first, second and third frequencies should preferably be one at which the resistance component reaches approximately its maximum, one at which the resistance component reaches approximately its minimum and one at which the absolute value of the reactance component reaches approximately its maximum. To suppress adverse influence of stray capacitances and foreign noises to simplify the analog circuit, as for the first, second and third frequencies, preferably they are selected to be as low as possible, e.g. in the range of 1 kHz to 100 kHz. For example, the first frequency is 4 kHz, the second frequency is 16 kHz and the third frequency is 64 kHz.

Then the vector impedance locus and the parameters associated thereto are calculated based on the measured values by the alternating current with respective frequencies.

Figure 3:
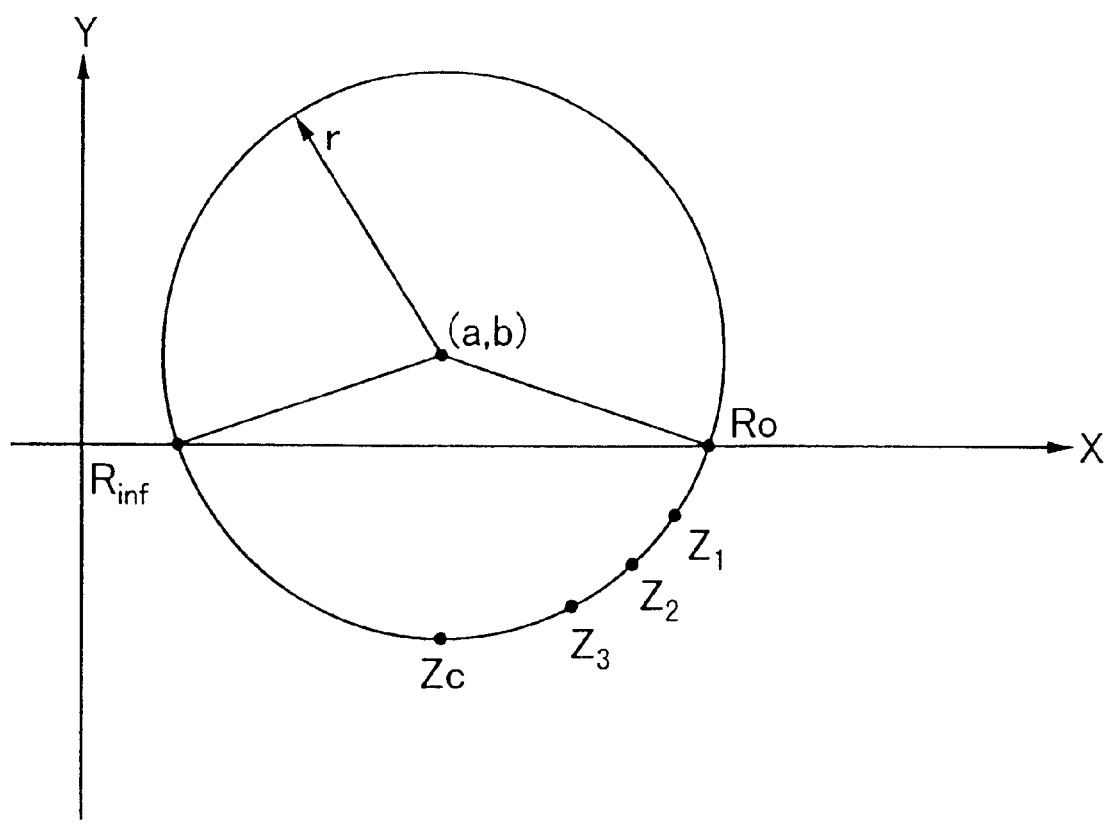
FIG. 3 is a graphical representation illustrating a relation between a point of characteristic frequency and points of 0 and infinite frequencies.

According to an assumption that the vector impedance locus derived is a circular arc, the bioelectrical impedance values Z1, Z2 and Z3 measured respectively at the first, second and third frequencies (hereinafter referred to as F1, F2 and F3) are on a circular arc of a certain circle as shown in FIG. 3. Herein, a real axis (axis of abscissa) and an imaginary axis (axis of ordinate) of the vector impedance plane are described as an X-axis and a Y-axis respectively. Therefore, an equation of the circle having these three points thereon is described as:

$$(X-a)^2+(Y-b)^2=r^2 \quad (1)$$

where, "a" is X coordinate of the center of the circle, "b" is Y coordinate of the center of the circle, and "r" is radius of the circle. The values "a", "b", and "r" can be calculated by substituting the measured values of the bioelectrical impedance vector Z1, Z2 and Z3 at the frequencies F1, F2 and F3 in the equation (1).

Intersections of the circle and X-axis or the real axis are determined by the equation (1) as:

$$X=a\pm\sqrt{(r^2-b^2)}$$

wherein, since $R^0 > R_{inf}$, $$R_0 = a + \sqrt{(r^2-b^2)}$$

$$R_{inf} = a - \sqrt{(r^2-b^2)}$$

Figure 1:
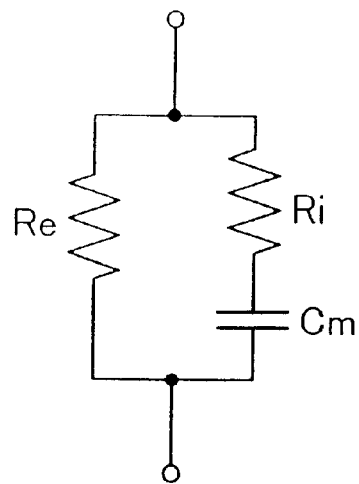
FIG. 1 shows an electrically equivalent circuit of a cell in a tissue.
Figure 2:
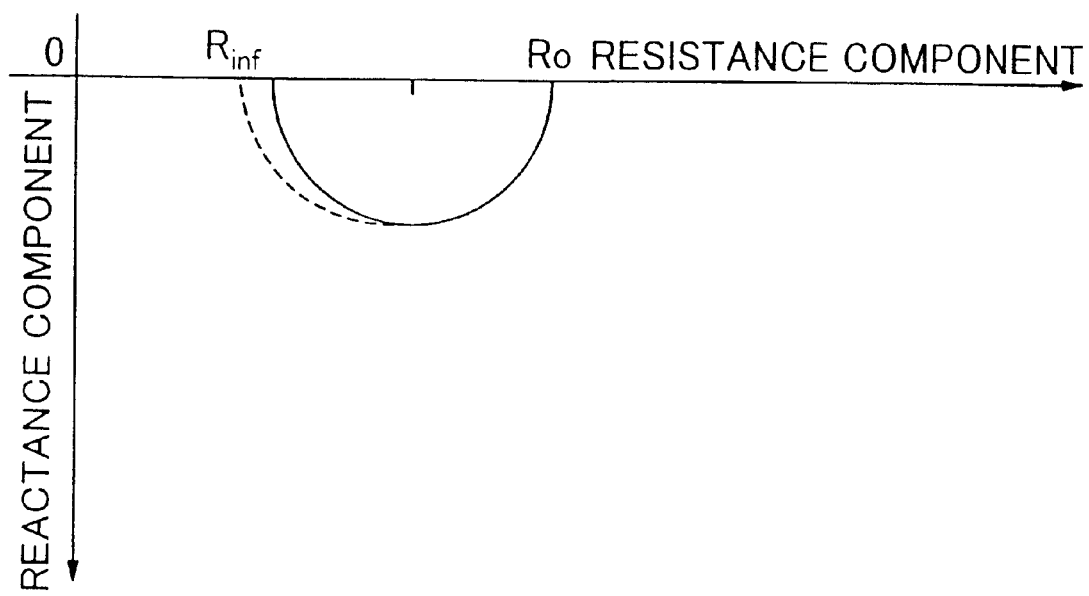
FIG. 2 is a graphical representation of a bioelectrical vector impedance locus of a human body.

Accordingly, Re and Ri of the equivalent circuit of FIG. 1 are described as:

$$Re=R^0$$

$$Ri=R_0 \cdot R_{inf}/(R_0-R_{inf})$$

Since the impedance vector Zc at the characteristic frequency Fc is defined by a point where the reactance or the imaginary axis component, that is, the absolute value of Y-axis component, takes a maximum value, X coordinate as a real axis component and Y coordinate as an imaginary axis component of the impedance vector Zc are determined as:

$$X=a, Y=b-r$$

and thereby the impedance vector Zc is represented as:

$$Zc=Rc+jXc=a+j(b-r)$$

where Rc is a resistance component of Zc, and Xc is a reactance component of Zc.

According to Cole-Cole model described in DESCRIPTION OF THE PRIOR ART, the impedance vector at a frequency ω is represented as:

$$Z(\omega)=R_{inf}+(R_0-R_{inf})/(1+(j\omega\tau)\beta)$$

where, $Z(\omega)$ is the impedance vector at ω, and τ and β are constants.

When $\tau=1/\omega c$, $$Z(\omega)=R_{inf}+(R_0-R_{inf})/(1+(j\omega/\omega c)\beta)$$

where $\omega c=2\pi Fc$.

Fc and β can be calculated also based on these relations and a data on the circle.

Then the body composition values including the extra-cellular water (ECW), the intra-cellular water (ICW), a ratio of the extra-cellular water to the intra-cellular water, the total body water (TBW), the fat free mass (FFM), body fat mass (FM) and the body fat rate are calculated based on the vector impedance locus and the associated parameters, such as $R_0$, $R_{inf}$, Ri, Zc, Fc or the like, which are calculated beforehand (step S9). When the personal parameter has not been set, this process is omitted as described above.

Then the measured results and other results calculated based thereon are indicated on the indicator 6 (step S10). An example of the indication is shown in FIG. 7. Further, based on the measurement control parameter, the measured results, the arithmetic results, the parameters regarding the measurement or the like are transmitted to the external device through the external input/output interface 7 (step S11) or are stored in the auxiliary storage 5 (step S12).

After the above steps are completed, the process enters a wait state (step S13). When a re-measurement key is pushed (step S14), the measurement is performed again, and when a new-measurement key is pushed (step S15), the process returns to the step for personal parameter input and enters a wait state.

Figure 8:
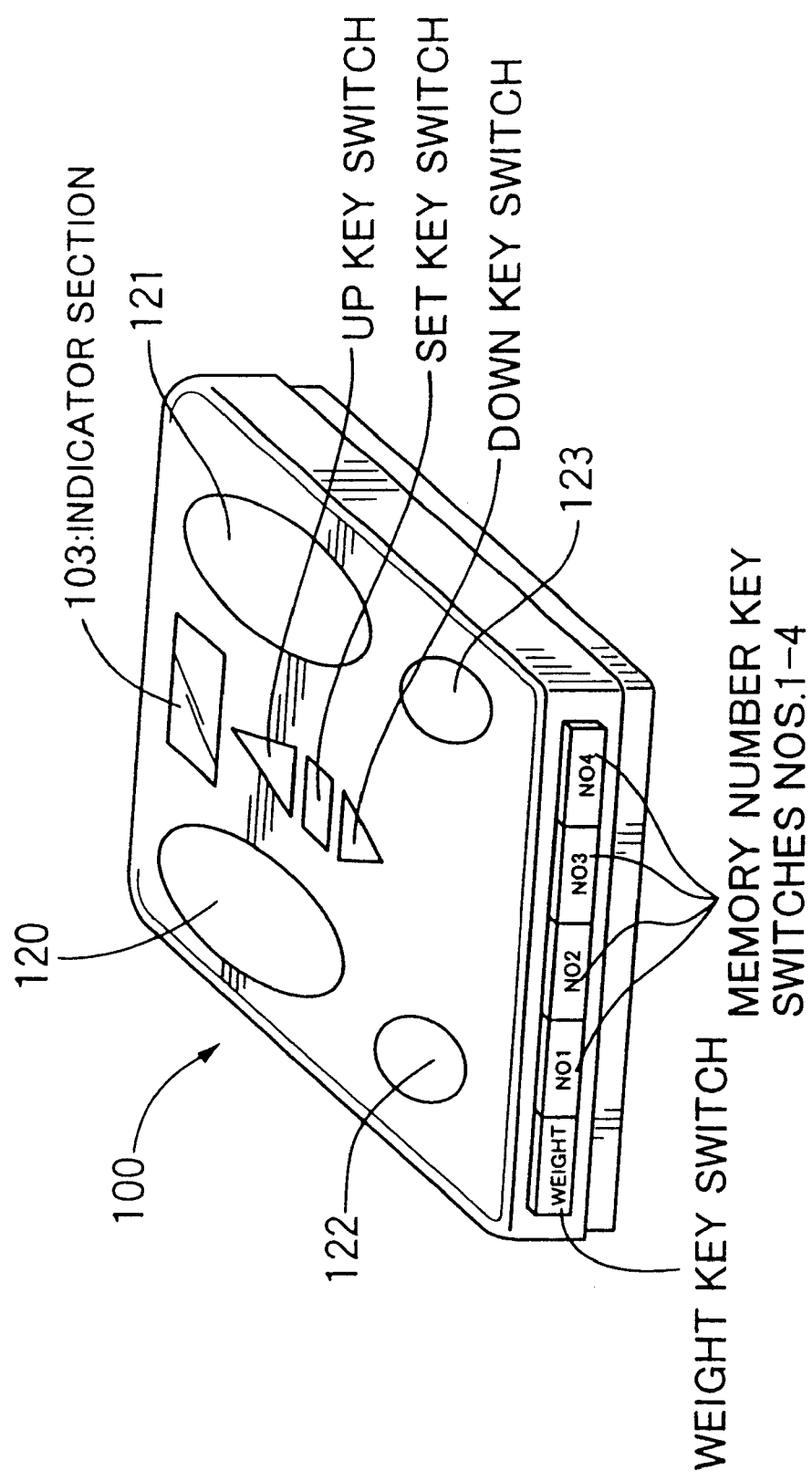
FIG. 8 is a schematic perspective view of a body composition measuring apparatus implementing a bioelectrical impedance measuring method according to another embodiment of the present invention.
Figure 9:
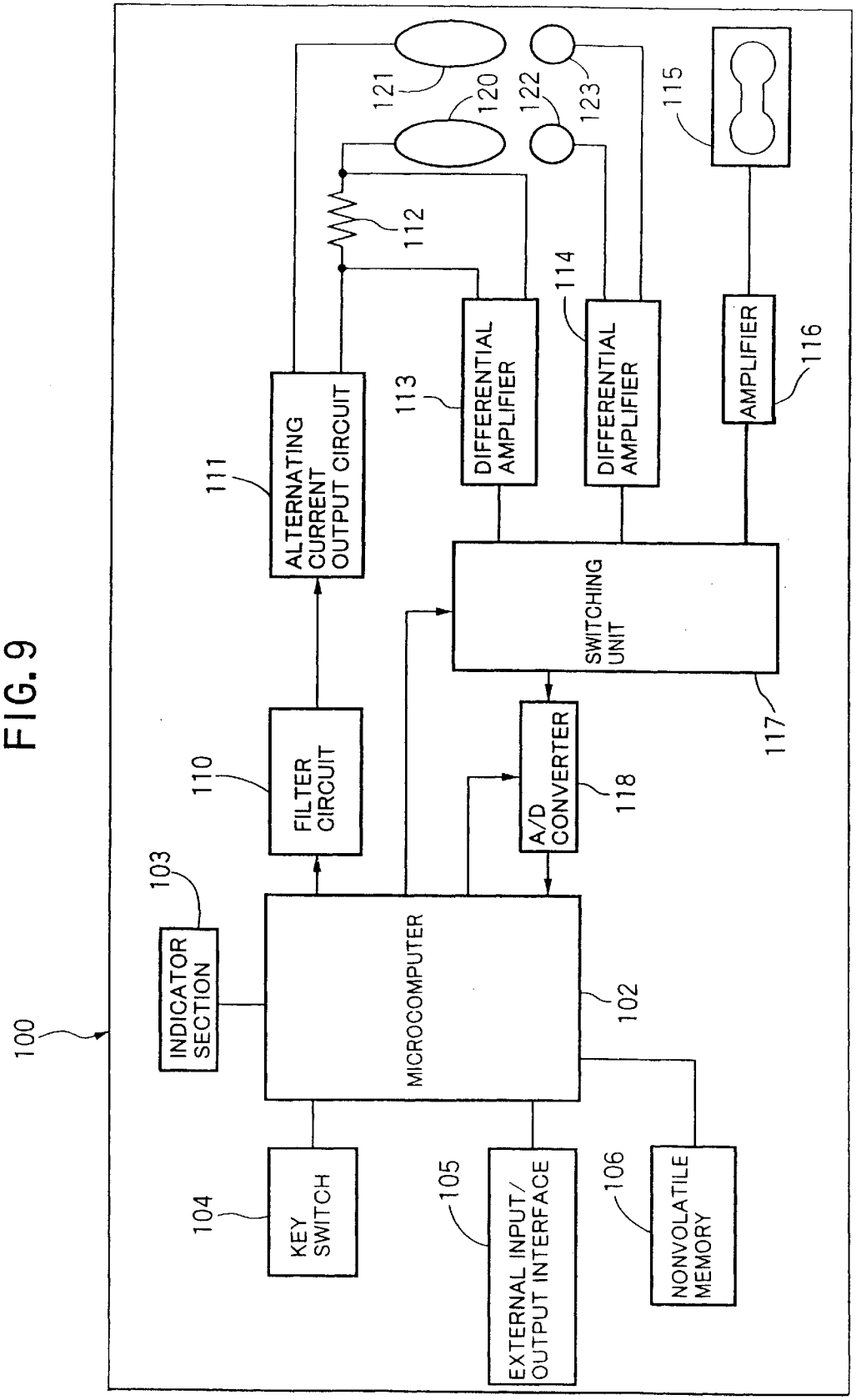
FIG. 9 is a schematic block diagram illustrating a general configuration of the apparatus of FIG. 8.

FIG. 8 is a schematic perspective view of a body composition measuring apparatus for executing a bioelectrical impedance measuring method according to another embodiment of the present invention, and FIG. 9 is a block diagram illustrating a general configuration of this apparatus. The apparatus of the present invention is, as shown in FIG. 8, a simplified apparatus incorporating a weight scale therein.

Main functional sections of the present apparatus 100 will be described with reference especially to FIG. 9.

The apparatus 100 comprises a microcomputer 102 having a functions of CPU, ROM, RAM, timer, I/O port or the like; an indicator section 103 for indicating a personal parameter setting of a person to be measured, a measured result, a condition during measurement or the like; a key switch 104 for inputting the personal parameter, and for selecting the personal parameter stored in a nonvolatile memory 106 or the like; an external input/output interface 105 for performing input/output operation with an external device; the nonvolatile memory 106 for storing a measurement control parameter, the personal parameters or the like; a filter circuit 110 for shaping an output signal from the microcomputer 102 into a signal to be applied to a living body; an alternating current output circuit 111 for applying an output signal from the filter circuit 110 to the person to be measured, with a constant effective value; a reference resistor 112 connected to an end of an output of the alternating current output circuit 111, for detecting a current applied to the person to be measured; a measuring current supply electrode 120 connected through the reference resistor 112 to one output terminal of alternating current output circuit 111; a measuring current supply electrode 121 connected to the other output terminal of alternating output circuit 111; a differential amplifier 113 for detecting a potential difference between ends of the reference resistor 112; potential measuring electrodes 122 and 123 for detecting potentials of the person to be measured at two points thereof; a differential amplifier 114 connected to the potential measuring electrodes 122 and 123 for detecting a potential difference therebetween; a weight sensor 115 for detecting a loading; an amplifier 116 for amplifying a signal from the weight sensor 115; a switching unit 117 for selectively outputting one of the outputs from the differential amplifiers 113, 114 and that from the amplifier 116 based on the control of the microcomputer 102; and an A/D converter 118 for converting an analog signal output from the switching unit 117 into a digital signal to output it to the microcomputer 102.

Figure 10:
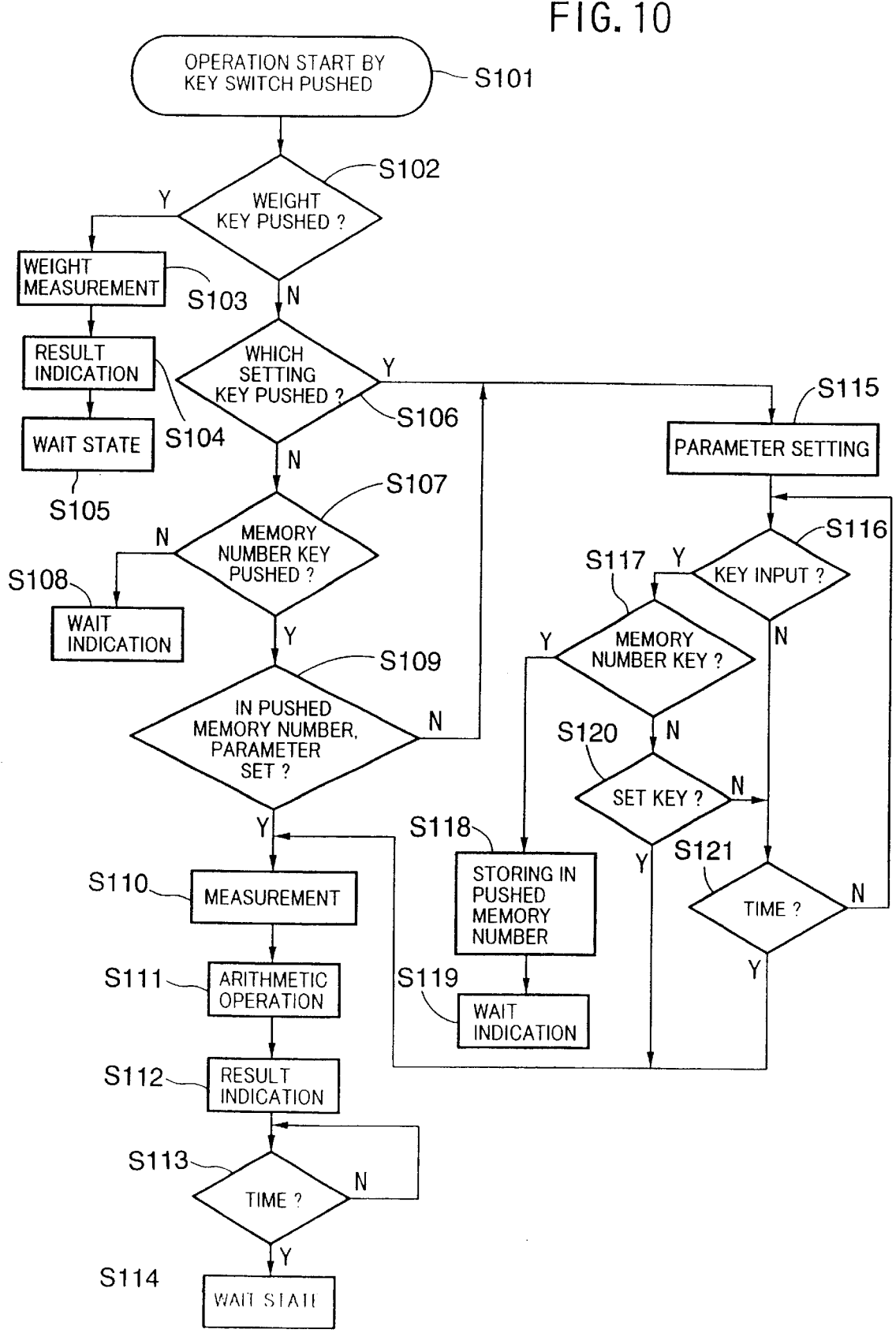
FIG. 10 is a flow chart illustrating a measuring procedure of the apparatus of FIG. 8.

Then an operation and an operating procedure of the present embodiment will be described with reference to FIG. 10, which is a flow chart generally illustrating the operation and the operating procedure of the present embodiment.

The operation of the present apparatus starts upon the key switch being pushed (step S101). The key switch used in the present embodiment includes eight key switches consisting of three key switches, that is, SET key, UP key and DOWN key used for setting the personal parameter; four key switches from No. 1 to No. 4 memory number key switches; and one key switch for performing only a body weight measurement. The operation of the present apparatus is branched into three ways depending on the kinds of the key switches pushed for starting the operation.

1. When the Body Weight Key is Pushed to Start the Operation (Step S102):

Only the body weight measurement is performed (step S103), a result thereof is indicated on the indicator section 103 (step S104), the indication is turned off after a certain period, and then the process enters a wait state (step S105) to wait a next key switch input.

When the body weight key is not pushed at step S102, it is judged whether any one of the setting keys (SET key, UP key, DOWN key) is pushed (step S106).

When none of the setting keys is pushed, it is judged whether any one of the No. 1 to No. 4 memory number keys is pushed (step S107). When none of the No. 1 to No. 4 memory number key switches is pushed, the process enters the wait state (step S108) to wait the next key switch input.

2. When the Memory Number Key Switch is Pushed to Start the Operation (Step S109):

The operation depends on whether the parameter has been set or not.

2-1. When the Personal Parameter Corresponding to the Pushed Memory Number Has Not Been Stored:

The same operation with that described in the following item 3. "When any one of the setting keys is pushed to start the operation" is performed. The personal parameter set at that time is stored as a data for the pushed memory number.

2-2. When the Personal Parameter Corresponding to the Pushed Memory Number Has Been Stored:

The personal parameter corresponding to the pushed memory number stored in the nonvolatile memory 106 is indicated on the indicator section 103 for a certain period and then the body weight is measured. At that time, in order to measure the body weight, the signal to be supplied from the microcomputer 102 to the filter circuit 110 when the impedance is to be measured is stopped and the switching unit 117 is controlled by the microcomputer 102 so that the output from the amplifier 116 may be selected as the input to the A/D converter 118.

After the body weight is measured, the bioelectrical impedance is measured. At that time, according to the measurement control parameter having been written beforehand in the ROM in the microcomputer 102, the signal is supplied from the microcomputer 102 to the filter circuit 110 and the output therefrom is input to the alternating current output circuit 111. The output from the alternating current output circuit 111 is applied to the person to be measured through the reference resistor 112 connected to one end of the alternating current output circuit 111. Since the potential difference signal of the reference resistor 112 and the potential difference signal between two points of the living body are output respectively from the differential amplifiers 113 and 114, they are converted into the control signal for the microcomputer 102 and are output to the microcomputer 102. The measurement of the bioelectrical impedance described above is performed based on the measurement control parameter for each of three frequencies including the first, the second and the third frequencies (step S110).

An arithmetic processing is performed using the measured bioelectrical impedance data to determine $R_0$, $R_{inf}$ and Zc and further to calculate Re and Ri in the same manner as described with reference to the embodiment mentioned above. The extra-cellular water, the intra-cellular water, the total body water, the fat free mass, and the body fat mass are determined based on these calculated results (step S111).

The results of the arithmetic processing are indicated on the indicator section 103 (step S112), the indication is turned off after a certain period (step S113), and the process enters the wait state (step S114) to wait the next key switch input.

The second full paragraph on page 17 now reads as follows:
3. When Any One of the Setting Keys is Pushed at Step S106 to Start the Operation:

An indicating for setting the personal parameter is indicated on the indicator section 103 (step S115). In the present embodiment, items of the personal parameter to be set are two items, that is, the sex and the height. Each item of the personal parameters is to be set according to the indication on the indicator section 103. When the setting value is input, the UP key and the DOWN key are used to select a selection item and a value to be set. The sex and the value of the height are confirmed and set by pushing the SET key when being input respectively.

At that time, in case where the process branches off from the above item 2-1 "When the personal parameter corresponding to the pushed memory number has not been stored" to the present setting step of the personal parameter, the personal parameter set herein is automatically stored in the nonvolatile memory 106 as a data for the memory number having been pushed (step S118), the indication is turned off after a certain period, and the process enters the wait state (step S119) to wait the next key switch input.

In other cases, he process enters the wait state to wait the key input for a certain period (step S116).

When the memory number key switch is pushed during the certain period (step S117), the personal parameter set herein is stored in the nonvolatile memory 106 as a data for the pushed memory number (step S118), the indication is turned off after a certain period, and the process enters the wait state (step S119) to wait the next key switch input.

Further, when the SET key is pushed during the certain period (step S120) or when the certain period has passed to end the wait state for waiting the next key input (step S121), the operation described in the above item 2 "When the memory number key switch is pushed to start the operation" (step S110 et seq.) is performed.

Although the external input/output interface 105 is not referred to in the description of the main operation and the operating procedure, in the present embodiment, this device is added when it is necessary and has functions to output the measured result of the bioelectrical impedance and the results derived therefrom through the arithmetic processing and to input a measurement control command or the parameters from an external device into the present apparatus.

Since the number of frequencies used for the measurement is limited to three, an analog circuit section for measuring the impedance can be made simpler comparing with the conventional one.

Since the present apparatus does not require such a lot of iterative operations for constructing the vector impedance locus as the conventional one, a high speed arithmetic unit and a peripheral device thereof are not necessary. In addition, the period for the measurement is made short, which allows a user (patient) to use it comfortably.

Since the present apparatus is simplified as a whole comparing with the conventional one, the apparatus can be made compact and the cost thereof can be reduced.

Since the compactness of the present apparatus allows it to be driven by battery, only a small area is necessary to install it and this makes it possible to be carried easily.

Further, since the present apparatus can be made compact and can be manufactured at low cost, as shown in above another embodiment, it can be spread in the same manner as of the conventional body fat meter with single frequency measurement system while allowing more accurate measurement of body fat comparing with the conventional one with single frequency measurement system.

That is, when the present apparatus is to be configured incorporating a body weight measuring section therein, what has to be made is only to add a small modification to a circuit section of the conventional body weight scale with body fat meter.

What is claimed is:

1. A method for measuring a bioelectrical impedance of a patient by applying alternating current to a body of said patient, said method comprising the steps of:
   determining a first bioelectrical impedance value using an alternating current having a first frequency;
   determining a second bioelectrical impedance value using an alternating current having a second frequency;
   determining a third bioelectrical impedance value using an alternating current having a third frequency; and
   determining a vector impedance locus by assuming that the vector impedance locus is a circular arc, substituting the first, second and third bioelectrical impedance values in an equation of a circle, and solving simultaneous equations for an X coordinate of the center of the circle, a Y coordinate of the center of the circle and the radius of the circle, to determine bioelectrical impedance values at a zero frequency and at an infinite frequency.

2. A bioelectrical impedance measuring method in accordance with claim 1, wherein the bioelectrical impedance value $R_0$ at the zero frequency is described as $R_0 = a + \sqrt{(r^2 - b^2)}$ and the bioelectrical impedance value $R_{inf}$ at the infinite frequency is described as $R_{inf} = a - \sqrt{(r^2 - b^2)}$, where the X coordinate of the center of the circle forming said circular arc is a, the Y coordinate of the center of the circle is b, and the radius of the circle is r.

3. A bioelectrical impedance measuring method in accordance with claim 1, wherein each of said first, second and third frequencies are in the range of 1 kHz to 100 kHz.

4. A bioelectrical impedance measuring method in accordance with claim 1 wherein the first, second and third frequencies comprise one frequency at which a resistance component of said bioelectrical impedance reaches approximately its maximum, one frequency at which a resistance component of said bioelectrical impedance reaches approximately its minimum and one frequency at which an absolute value of the reactance component of said bioelectrical impedance reaches approximately its maximum.

5. A body composition measuring apparatus for measuring a bioelectrical impedance of a patient by applying alternating current to a body of said patient, said body composition measuring apparatus comprising:

an alternating current generating device for generating at least three alternating currents, each having different frequencies;

a measuring device for determining a first bioelectrical impedance value, a second bioelectrical impedance value and a third bioelectrical impedance value based on measurements using an alternating current having a first frequency, an alternating current having a second frequency and an alternating current having a third frequency, respectively, said alternating currents generated by said alternating current generating device;

an arithmetic device which derives a vector impedance locus from only said first, second and third bioelectrical impedance values, wherein the vector impedance locus is a circular arc, to determine bioelectrical impedance values at a zero frequency and at an infinite frequency; and a judging device which judges a body composition of said patient based on said bioelectrical impedance values determined by said arithmetic device.

6. A body composition measuring apparatus in accordance with claim 5, wherein the bioelectrical impedance value $R_0$ at the zero frequency is described as $R_0 = a + \sqrt{(r^2 - b^2)}$ and the bioelectrical impedance value $R_{inf}$ a the infinite frequency is described as $R_{inf} = a - (r^2 - b^2)$, where an X coordinate of the center of the circle forming said circular arc is a, a Y coordinate of the center of the circle is b, and the radius of the circle is r.

7. A body composition measuring apparatus in accordance with claim 5, further comprising:

an input device for entering a personal parameter including a body weight of said patient; and an indicating device which indicates information regarding said body composition judged by said judging device, wherein said judging device takes said personal parameter input via said input device into account when judging said body composition of said patient.

8. A body composition measuring apparatus in accordance with claim 5, further comprising:

a body weight measuring device for measuring a body weight of said patient;

an input device for entering a personal parameter other than said body weight of said patient; and an indicating device for indicating information regarding said body composition of said patient judged by said judging device, wherein said judging device takes said body weight measured by said body weight measuring device and said personal parameter input via said input device into account when judging said body composition of said patient.

9. A body composition measuring apparatus in accordance with any of claims 5 to 8, wherein each of said first, second and third frequencies are in the range of 1 kHz to 100 kHz.

10. A body composition measuring apparatus in accordance with any of claims 5 to 8 wherein the first, second and third frequencies comprise one frequency at which a resistance component of said bioelectrical impedance reaches approximately its maximum, one frequency at which a resistance component of said bioelectrical impedance reaches approximately its minimum and one frequency at which an absolute value of the reactance component of said bioelectric impedance reaches approximately its maximum.

11. A body composition measuring apparatus in accordance with any of claims 5 to 8, wherein said body composition includes at least one of an extra-cellular water mass, an intra-cellular water mass, a total body water mass, a fat free mass, and a body fat mass.

* * * * *